United States Patent [19]

Mondadori

[11] Patent Number: 4,746,670
[45] Date of Patent: May 24, 1988

[54] USE OF 2-AMINOALKYL-5-PYRIDINOLS AS NOOTROPIC AGENTS AND ANTIDEPRESSANTS

[75] Inventor: Cesare Mondadori, Aesch, Switzerland

[73] Assignee: Ciba-Geigy Corporation, Ardsley, N.Y.

[21] Appl. No.: 37,911

[22] Filed: Apr. 1, 1987

[30] Foreign Application Priority Data

Apr. 11, 1986 [CH] Switzerland ............... 1432/86

[51] Int. Cl.$^4$ ............................................. A61K 31/44
[52] U.S. Cl. ............................................. 514/347
[58] Field of Search ................................. 514/347

[56] References Cited

U.S. PATENT DOCUMENTS 4,260,619  4/1981  Mondadori .................. 424/263

Primary Examiner—Stanley J. Friedman
Attorney, Agent, or Firm—Irving M. Fishman; Michael W. Glynn

[57] ABSTRACT

The present invention relates to the use of secondary 2-aminoalkyl-5-pyridinols of the general formula I

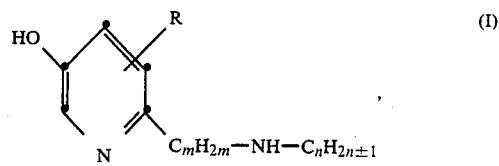

wherein R is hydrogen or lower alkyl, m is an integer from 2 to 4 and n is an integer from 1 to 7, and the acid addition salts thereof, as nootropic agents and antidepressants and for the preparation of pharmaceutical compositions having nootropic and antidepressant activity.

12 Claims, No Drawings

USE OF 2-AMINOALKYL-5-PYRIDINOLS AS NOOTROPIC AGENTS AND ANTIDEPRESSANTS

The present invention relates to the use of secondary 2-aminoalkyl-5-pyridonals of the general formula I

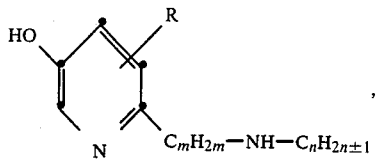

wherein R is hydrogen or lower alkyl, m is an integer from 2 to 4, and n is an integer from 1 to 7, or of therapeutically useful acid addition salts thereof, as effective nootropic and antidepressant agents for the therapeutic and preventive treatment of cerebral insufficiency.

The term "lower" used throughout this specification to qualify organic radicals or compounds indicates that said radicals or compounds contain not more than 7, preferably 4 and, most preferably, 1 or 2 carbon atoms.

A lower alkyl radical R may be in any of the free positions 2, 4 or 6 of the pyridine ring. The lower alkyl radical is e.g. ethyl, n-propyl or isopropyl, n-butyl or isobutyl, n-pentyl, n-hexyl, or n-heptyl, but is preferably methyl. However, the preferred meaning of R is hydrogen.

The alkylene group $C_mH_{2m}$ is preferably 1,2-propylene, but may also be ethylene, 1,3-propylene, 1,2-, 1,3- or 1,4-butylene.

The $C_nH_{2n+1}$ group is preferably lower alkyl, e.g. methyl, ethyl, n-propyl or isopropyl, n-, iso- or tert-(butyl, pentyl, hexyl, or heptyl). The preferred meaning is isopropyl.

The $C_nH_{2n-1}$ group is either lower alkenyl, e.g. allyl, methallyl, or 2- or 3-butenyl, 2- or 3-pentenyl, 2- or 3-hexenyl or 2- or 3-heptenyl, or also cyclised lower cycloalkyl, e.g. cyclopropyl, cyclobutyl, cyclopentyl, cyclohexyl or cycloheptyl, with cyclopropyl or cyclohexyl being preferred.

The compounds of formula I are known and have been described e.g. in European patent specification No. 19739 as having antihypertensive, in particular cardioprotective, properties, e.g. antischemic (i.e. antianginal) properties.

The acid addition salts of the dibasic compounds of formula I are preferably therapeutically useful acid addition salts. Acids from which the therapeutically useful salts are derived are e.g. inorganic acids such as hydrohalic acids, for example hydrochloric or hydrobromic acid, or sulfuric acid, phosphoric acid, nitric acid or perchloric acid; or organic acids such as aliphatic or aromatic carboxylic acids or sulfonic acids, e.g. formic acid, acetic acid, propionic acid, succinic acid, glycolic acid, lactic acid, fumaric acid, maleic acid, tartaric acid, citric acid, maleic acid, hydroxymaleic acid, pyruvic acid, phenylacetic acid, benzoic acid, 4-aminobenzoic acid, anthranilic acid, 4-hydroxybenzoic acid, salicyclic acid, pamoic acid, nicotinic acid, methanesulfonic acid, ethanesulfonic acid, hydroxyethanesulfonic acid, benzenesulfonic acid, halobenzenesulfonic acid, toluenesulfonic acid, naphthalenesulfonic acid, sulfanilic acid, cyclohexylsulfamic acid; or ascorbic acid. The salts are known and are disclosed e.g. in European patent specification No. 19739.

Surprisingly, it has now been found that the above mentioned compounds of formula I have nootropic and antidepressant activity and afford for example protection against the amnesiogenous action of cerebral electroshock and enhance memory performance as well as concentration. The vigilance stimulation, enhancement of concentration and antidepressant acitivity are allied to very good tolerance and very low toxicity.

On account of these properties, the compounds of formula I are suitable for the treatment of cerebral insufficiency, especially of impaired memory states of different provenance, insufficiency of vigilance regulation such as senile dementia, multi-infarction dementia or dementia of the Alzheimer type, and also sequels of cerebral traumas or apoplexy as well as senile depressions. The compounds are administered enterally or parenterally, preferably orally or intravenously, e.g. in gelatin capsules or in the form of starch-containing suspensions or aqueous solutions. The dose can be within the range from 1 to 30 mg/kg per day i.p. or from 10 to 100 mg/kg per day perorally.

The compounds of formula I also have a marked effect on the vigilance state of cats. Total sleeping time was shortened in accordance with the dose administered. The relative proportion of REM (rapid eye movement) sleep which is variously linked to memory activity was, interestingly, not diminished; on the contrary, it was substantially prolonged in comparison with the total sleeping time. This finding is all the more remarkable, as virtually all psychoactive substances shorten REM sleep.

To illustrate this invention, 2-(2-isopropylaminopropyl)-5-pyridinol monofumarate, which shortens the total sleeping time by 28% when adminstered in a dose of 10 mg/kg p.o. and by 54% when administered in a dose of 30 mg/kg p.o., is cited by way of example.

The present invention relates in particular to the use of compounds of formula I, wherein R is hydrogen or methyl, m is 2 or 3 and n is an integer from 2 to 6, and the acid addition salts thereof, in particular therapeutically useful acid addition salts, as nootropic agents and antidepressants, and to the preparation of a pharmaceutical composition having nootropic and mood-enhancing antidepressant activity.

More particularly, the invention relates to the use of compounds of formula II

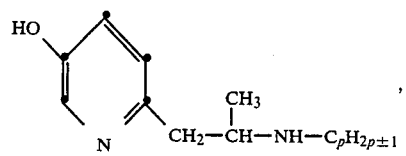

wherein p is an integer from 3 to 6, and the acid addition salts thereof, especially therapeutically useful acid addition salts thereof, as nootropic agents and for the preparation of a pharmaceutical composition having nootropic activity.

Most particularly, the invention relates to compounds of the general formula II, wherein $C_pH_{2p\pm1}$ is tert-butyl, allyl or cyclopropyl or, preferably, isopropyl, and the acid addition salts thereof, in particular pharmaceutically acceptable acid addition salts thereof, as nootropic agents and for the preparation of a pharmaceutical composition having nootropic activity.

The preparation of the compounds of formula I and/or II is described in detail e.g. in European patent specification No. 19739.

The compounds of formulae I and II can be used for the preparation of pharmaceutical compositions which contain an effective amount of active substance together, or in admixture, with carriers, and which are suitable for enteral or parenteral administration. It is preferred to use tablets or gelatin capsules that contain the active ingredient together with diluents, for example lactose, dextrose, saccharose, mannitol, sorbitol, cellulose and/or glycine, and/or lubricants, for example silica, talcum, stearic acid or salts thereof, such as magnesium or calcium stearate, and/or polyethylene glycol. Tablets can also contain binders, for example magnesium aluminium silicate, starch paste, gelatin, tragacanth, methyl cellulose, sodium carboxymethyl cellulose and/or polyvinylpyrrolidone, and, if desired, disintegrators, for example starches, agar, alginic acid or a salt thereof, such as sodium alginate, and/or effervescent mixtures, or adsorption agents, colorants, flavouring matters and sweeteners. Injectable preparations are preferably isotonic aqueous solutions or suspensions. The pharmaceutical preparations can be sterilised and/or contain adjuvants, for example preservatives, stabilisers, wetting agents and/or emulsifiers, solubility promoters, salts for regulating the osmotic pressure and/or buffers. The pharmaceutical compositions of the invention which, if desired, can contain further pharmacologically useful substances, are prepared in known manner, for example using conventional mixing, granulating or confectioning methods, and they contain from about 1% to 75%, especially from 10% to 50%, of the active ingredient.

The invention is illustrated by the following Examples.

EXAMPLE 1

Reduction of the amnesiogenous action of a cerebral electroshock [method of Mondadori, C. and Classen, W., Acta Neurol. Scand. 69, Suppl. 99, 125-129 (1984)]

The test equipment consists of a large box (35×20×10 cm) which is connected by means of a sliding door to a small box (10×10×18 cm). The small box is brightly lit from above by a 100 watt lamp, whereas the large box is dark. The floor of both compartments consits of an electrifiable grating, the rods of which (diameter: 6 mm) are each spaced 13 mm apart.

For treatment, male mice having a body weight of 20-22 g are put individually, in groups of 10, into the brightly lit small box. As mice have an instinctive preference for the dark, they usually go into the dark compartment within 30 seconds. As soon as all the mice have entered this compartment, the sliding door is closed and a shock (1 mA, 5 seconds) is administered to the paws of the mice. The animals are then immediately taken out of the testing unit. Two separate assays are carried out (in the morning between 8 and 11 a.m. and in the afternoon between 12 noon and 3 p.m.).

To test the learning performance (retest), the mice are once more put individually into the lit compartment and the time until they are all in the dark is measured. Most of the animals will now normally remain in the lit compartment over the entire observation time of 150 seconds.

The learning performance is substantially annulled, i.e. the memory of the shock to the feet is at least partially extinguished if, as amnesiogenous treatment, a brief electroshock treatment follows directly on the shock to the feet adminstered in the training run. Parameters of the electroshock: 50 mA, 0.4 sec., 50 Hz.

For testing and comparing the protective action agaist the amnesiogenous action of the electroshock, the animals are divided into different groups and the test compounds are administered intraperitoneally 30 minutes before the training procedure, in doses of 0.1, 1, 10 and 30 mg/kg (using 10 mice for each dose), as solutions in 0.5% methyl cellulose (methocel), with methocel alone (=placebo) being administered to control groups, and the animals are subjected to electroshock treatment immediately after training. The degree of the learning performance still retained is measured 24 hours later from the residence time in the lit box and compared with that obtained with the other test substances, as well as from control animals to which methocel only has been administered, and which have been subjected to training without and with subsequent electroshock treatment. A group of mice that received placebo and which was not subjected electroshock treatment was used as control group for assessing learning in the avoidance test, and a second control group treated with placebo and then subjected to electroshock was used to determine the extent of the amnesiogenous action of the electroshock treatment.

The above activities can be observed for example after administration of 0.1 mg/kg of 2-(2-isopropylaminopropyl)-5-pyridinol monofumarate.

EXAMPLE 2

Measuring the enhancement of memory performance [method of Mondadori, C., step-down passive avoidance test, Psychopharmacol. 63, 297-300 (1979)]

The test equipment consists of a box (50×50×50 cm) which is illuminated normally by daylight and which is fitted with a grating whose rods (4 mm in diameter) are each spaced 13 mm apart. A wooden platform is positioned in the centre of the grating and is surrounded by a plastic tube (18 cm high, 68 mm in diameter). For training, groups of 50 male mice having a body weight of 20-22 g are used by placing one animal at a time on the platform surrounded by the plastic tube, removing the plastic tube after 10 seconds, and measuring the time needed by the animal to step down and touch the grating with all four paws. When all 4 paws are in contact with the grating, a shock is administered (1 mA, 50 Hz, 1 second).

To test the learning effect (retest), the mice are again placed individually after 24 hours on the platform surrounded by the plastic tube.

To test and compare the enhancement of memory performance, the test compounds are administered intraperoneally in doses of 0.3, 3 and 30 mg/kg (using 50 mice for each dose) in the form of suspensions in 0.5% methyl cellulose (methocel) to the individual groups of test animals 30 and 60 minutes before training or within 60 seconds after electroshock treatment to the paws, with methocel alone being administered as placebo to control animals. Administration is made either 30 minutes (i.p.) or 60 minutes (p.o.) before or immediately after the test. The degree of enhancement or impariment of the learning effects is assessed 24 hours later from the time each individual animals remains on the platform as compared with control animals to which only the solvent was administered. An enhancement of memory performance can be established as follows, e.g. by intraperoneal administration of 2-(2-isopropylaminopropyl)-5-pyridinol monofumarate before or after training:

| (a) before the test | |
|---|---|
| dose | test latencies (sec) |
| 0.3 mg/kg i.p. | 35.3 ± 5.8[xx] |
| 3.0 mg/kg i.p. | 38.0 ± 5.9[xx] |
| 30.0 mg/kg i.p. | 56.5 ± 7.9[xxx] |
| control group | 26.6 ± 5.5 |
| (b) immediately after the test | |
| dose | test latencies (sec) |
| 0.3 mg/kg i.p. | 51.8 ± 7.6[xx] |
| 3.0 mg/kg i.p. | 46.4 ± 7.2[xx] |
| 30.0 mg/kg i.p. | 44.2 ± 6.8[xx] |
| control group | 28,5 ± 5,2 |

[xx] $p < 0.01$
[xxx] $p < 0.001$ (Mann-Whitney U-test)

The results show that the learning performance is enhanced by 78% by administration of the above compound in a dose of 0.3 mg/kg i.p. immediately after the test, and by 32% when administration is made before the test. These effects are statistically highly significant.

EXAMPLE 3

Preparation of 10,000 tablets each containing 10 mg of active ingredient

Composition:
2-(2-isopropylaminopropyl)-5-pyridinol dihydrochloride: 100 g
lactose: 3435 g
corn starch: 125 g
polyethylene glycol 6000: 150 g
talcum: 150 g
magensium stearate: 40 g
purified water: q.s.

Procedure: All the powdered constituents are sieved through a sieve having a mesh size of 0.6 mm. The active ingredient is then mixed with lactose, talcum, magnesium stearate and half of the starch in a suitable mixer. The other half of the starch is suspended in 65 ml of water and the suspension is added to a boiling solution of polyethene glycol in 260 ml of water. The resultant paste is added to the powders and granulated, optionally with the further addition of water. The granulate is dried overnight at 35° C., sieved through a sieve having a mesh size of 1.2 mm, and compressed to tablets of 10.3 mm diameter with a breaking notch.

EXAMPLE 4

Preparation of 1000 capsules each containing 50 mg of active ingredient

Composition:
2-(2-isopropylaminopropyl)-5-pyridinol monofurmarate: 50 g
corn starch: 5 g
lactose: 143.75 g
magensium stearate: 1 g
wetting agent: 0.25 g Procedure: All the powdered constituents are sieved through a sieve having a mesh size of 0.6 mm. The active ingredient is homogenised in a suitable mixer first with magnesium stearate and wetting agent and then with starch and lactose. No. 2 capsules are each filled with 200 mg of the mixture in a filling machine.

Tablets or capsules containing another compound of formula I are prepared in analogous manner.

What is claimed is:

1. A method of treating a depressive condition or a nootropically active agent responsive condition in a mammal in need thereof, comprising administering to said mammal an antidepressively or nootropically effective amount of a secondary 2-aminoalkyl-5-pyridinol of the general formula I

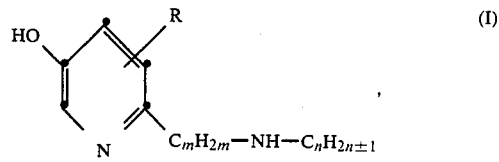

wherein R is hydrogen or lower alkyl, m is an integer from 2 to 4 and n is an integer from 1 to 7, or an acid addition salt thereof.

2. A method according to claim 1, wherein R is hydrogen or methyl or an acid addition salt thereof.

3. A method according to claim 1, wherein R is hydrogen or methyl, m is 2 or 3 and n is an integer from 2 to 6, or an acid addition salt thereof.

4. A method of treating a depressive condition or a nootropically active agent responsive condition in a mammal in need thereof, comprising administering to said mammal an antidepressively or nootropically effective amount of a compound of the general formula II

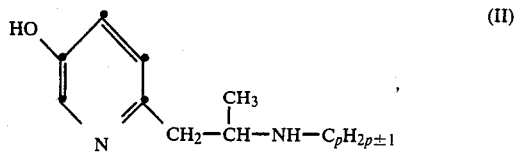

wherein p is an integer from 3 to 6, or an acid addition salt thereof.

5. A method according to claim 4, wherein $C_pH_{2p+1}$ is isopropyl or tert-butyl, or an acid addition salt thereof.

6. A method according to claim 4, wherein $C_pH_{2p+1}$ is isopropyl tert-butyl, allyl or cyclopropyl, or an acid addition salt thereof.

7. A method of treating a depressive condition or a nootropically active agent responsive condition in a mammal in need thereof, comprising administering to said mammal an antidepressively or nootropically effective amount of 2-(2-isopropylaminopropyl)-5-pyridinol, or an acid addition salt thereof.

8. A method of treating cerebral insufficiency or for regulating vigilance in a mammal, comprising administering to said mammal a nootropically or antidepressively effective amount of a compound of formula I

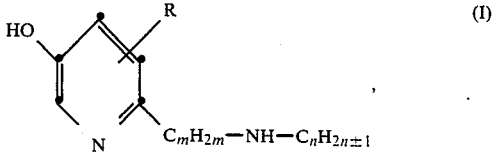

wherein R is hydrogen or lower alkyl, m is an integer from 2 to 4 and n is an integer from 1 to 7, or an acid addition salt thereof.

9. A method of treating cerebral insufficiency or for regulating vigilance in a mammal, comprising administering to said mammal a nootropically or antidepressively effective amount of a compound of formula I according to claim 8, wherein R is hydrogen or methyl, m is 2 or 3 and n is an integer from 2 to 6, or an acid addition salt thereof.

10. A method of treating cerebral insufficiency or for regulating vigilance in a mammal, comprising administering to said mammal a nootropically or antidepressively effective amount of a compound of formula II

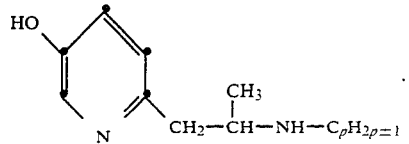

(II)

wherein p is an integer from 3 to 6, or an acid addition salt thereof.

11. A method of treating cerebral insufficiency or for regulating vigilance in a mammal, comprising administering to said mammal a nootropically or antidepressively effective amount of a compound of formula II according to claim 10, wherein $C_pH_{2p+1}$ is isopropyl, tert-butyl, allyl or cyclopropyl, or an acid addition salt thereof.

12. A method of treating cerebral unsufficiency or for regulating vigilance in a mammal, comprising administering to said mammal a nootropically or antidepressively effective amount of 2-(2-isopropylaminopropyl)-5-pyridinol or an acid addition salt thereof.

* * * * *